(12) United States Patent
Manstein et al.

(10) Patent No.: US 7,942,153 B2
(45) Date of Patent: May 17, 2011

(54) METHOD AND APPARATUS FOR DERMATOLOGICAL TREATMENT

(75) Inventors: Dieter Manstein, Boston, MA (US); R. Rox Anderson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/931,232

(22) Filed: Oct. 31, 2007

(65) Prior Publication Data
US 2008/0058784 A1    Mar. 6, 2008

(51) Int. Cl.
*A61B 19/00* (2006.01)
(52) U.S. Cl. ............................................. 128/898; 606/9
(58) Field of Classification Search ............. 607/88–91, 607/96, 101; 606/3, 8, 9, 131, 167; 128/898
See application file for complete search history.

(56) References Cited

U.S. PATENT DOCUMENTS

| | | | |
|---|---|---|---|
| 5,569,242 A | 10/1996 | Lax et al. | |
| 5,643,252 A | 7/1997 | Waner et al. | |
| 5,755,753 A | 5/1998 | Knowlton | |
| 5,879,326 A | 3/1999 | Godshall et al. | |
| 5,919,219 A | 7/1999 | Knowlton | |
| 5,948,011 A | 9/1999 | Knowlton | |
| 5,957,915 A * | 9/1999 | Trost ................ | 606/13 |
| 6,048,352 A | 4/2000 | Douglas et al. | |
| 6,083,196 A | 7/2000 | Trautman et al. | |
| 6,149,644 A * | 11/2000 | Xie ................... | 606/9 |
| 6,273,884 B1 | 8/2001 | Altshuler et al. | |
| 6,277,116 B1 | 8/2001 | Utely et al. | |
| 6,377,855 B1 | 4/2002 | Knowlton | |
| 6,405,090 B1 | 6/2002 | Knowlton | |
| 6,440,096 B1 * | 8/2002 | Lastovich et al. ............ | 604/27 |
| 6,497,719 B2 * | 12/2002 | Pearl et al. ................... | 607/89 |
| 6,511,475 B1 | 1/2003 | Altshuler et al. | |
| 6,591,124 B2 | 7/2003 | Sherman et al. | |
| 6,656,147 B1 | 12/2003 | Gertsek et al. | |
| 6,749,624 B2 | 6/2004 | Knowlton | |
| 6,766,202 B2 | 7/2004 | Underwood et al. | |
| 6,835,184 B1 * | 12/2004 | Sage et al. .................. | 604/46 |
| 6,855,131 B2 | 2/2005 | Trautman et al. | |
| 7,090,670 B2 * | 8/2006 | Sink .............................. | 606/9 |
| 7,186,235 B2 * | 3/2007 | Martin et al. ................. | 604/22 |
| 7,316,671 B2 * | 1/2008 | Lastovich et al. ............ | 604/290 |

(Continued)

FOREIGN PATENT DOCUMENTS
WO    00/78242    12/2000

(Continued)

OTHER PUBLICATIONS

Aplfelburg et al. "Dot or Pointillistic Method for Improvement in Results of Hypertrophic Scarring in the Argon Laser Treatment of Portwine Hemangiomas," Laser Surgery and Medicine 6:552-558 (1987).*

(Continued)

*Primary Examiner* — Ahmed M Farah
(74) *Attorney, Agent, or Firm* — Dorsey & Whitney LLP (57) ABSTRACT

The present invention provides improved methods and apparatus for skin treatment. The apparatus includes multiple sources of optical energy or several blades that are scanned along a region of skin to form micro-line patterns of damaged tissue. The micro-lines are small in at least one dimension, having a width of less than about 1 mm, and the wounded regions promote beneficial results by stimulation of wound healing and tissue remodeling.

25 Claims, 7 Drawing Sheets

U.S. PATENT DOCUMENTS

| | | |
|---|---|---|
| 2003/0032950 A1 | 2/2003 | Altshuler et al. |
| 2003/0199811 A1 | 10/2003 | Sage et al. |
| 2003/0216719 A1* | 11/2003 | Debenedictis et al. ......... 606/10 |
| 2005/0222565 A1 | 10/2005 | Manstein |

FOREIGN PATENT DOCUMENTS

| | | |
|---|---|---|
| WO | 02/053050 | 7/2002 |
| WO | 2004/086947 | 10/2004 |

OTHER PUBLICATIONS

Manstein et al., "Fractional Thermolysis: A New Concept for Cutaneous Remodeling Using Microscopic Patterns of Thermal Injury," Lasers in Surgery and Medicine, 9999:1-13 (2004).

Australian Examination Report dated Jan. 11, 2010 for Australian Patent application No. 2005231470.

* cited by examiner

METHOD AND APPARATUS FOR DERMATOLOGICAL TREATMENT

RELATED APPLICATIONS

This application claims priority to U.S. Provisional Application Ser. No. 60/558,397, filed on Apr. 1, 2004, and to U.S. Provisional Application Ser. No. 60/558,476, filed on Apr. 1, 2004.

INCORPORATION BY REFERENCE

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention is directed to an improved method for skin treatment. More specifically, it is directed to a method termed "fractional resurfacing" that uses electromagnetic radiation produced by one or more individual point sources or mechanical means to damage selected regions of the skin and thereby promote beneficial results by stimulation of wound healing and tissue remodeling.

BACKGROUND OF THE INVENTION

Skin is primarily made of two layers. The outer layer, or epidermis, has a depth of approximately 100 μm. The inner layer, or dermis, has depth of approximately 3000 μm from the outer surface of the skin. In the present disclosure, 'dermal tissue' refers to both the dermis and the epidermis. The term 'dermal tissue' is also used interchangeably with the term 'skin' herein.

There is ongoing demand for procedures to improve skin defects. Such improvements may involve, but are not limited to, reducing wrinkles or reducing dyschromia (any abnormality or irregularity of skin color resulting either from irregular pigment distribution or dilatated blood vessels). Various techniques providing this objective have been introduced in recent years. The different techniques can be generally categorized into two groups of treatment modalities: ablative laser skin resurfacing ("LSR") and non-ablative collagen remodeling ("NCR"). The first group of treatment modalities, LSR, includes causing fairly extensive thermal damage to the epidermis and/or dermis, while the second group, NCR, is designed to avoid thermal damage of the epidermis.

Figure 1:
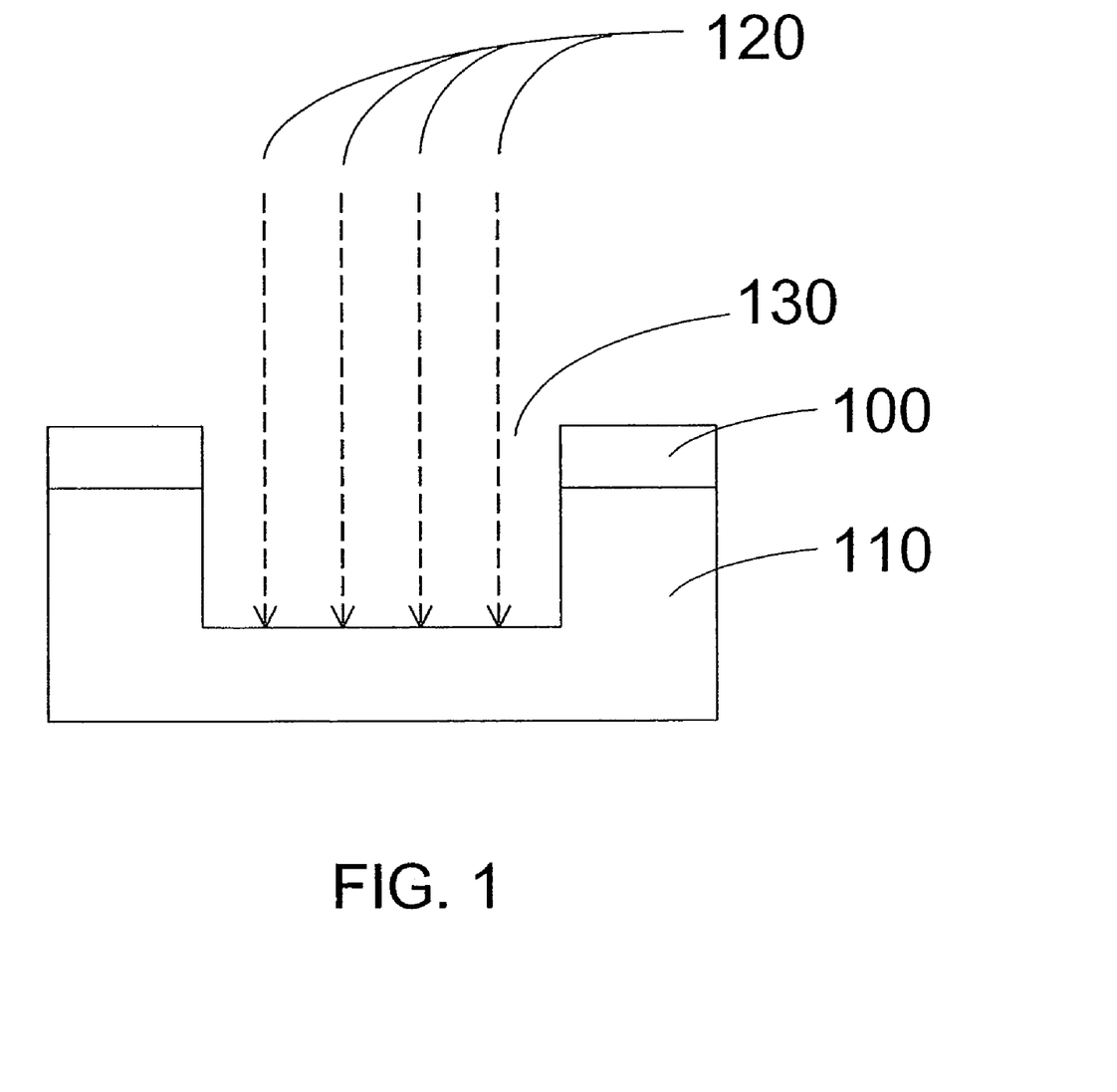
FIG. 1 is a schematic drawing of a cross section of a tissue treated using the LSR method.

LSR is considered to be an effective laser treatment for repairing skin. In a typical LSR procedure, shown schematically in FIG. 1, a region of the epidermis 100 and a corresponding region of the dermis 110 beneath it are thermally damaged to promote wound healing. Electromagnetic energy 120 is directed towards a region of skin, ablating the skin and removing both epidermal and dermal tissue in region 130. LSR with pulsed $CO_2$ or Er:YAG lasers, which may be referred to in the art as laser resurfacing or ablative resurfacing, is considered to be an effective treatment option for signs of photo aged skin, chronically aged skin, scars, superficial pigmented lesions, stretch marks, and superficial skin lesions. However, patients may experience major drawbacks after each LSR treatment, including edema, oozing, and burning discomfort during first fourteen (14) days after treatment. These major drawbacks can be unacceptable for many patients. A further problem with LSR procedures is that the procedures are relatively painful and therefore generally require an application of a significant amount of analgesia. While LSR of relatively small areas can be performed under local anesthesia provided by injection of an anestheticum, LSR of relatively large areas is frequently performed under general anesthesia or after nerve blockade by multiple injections of anesthetic.

A limitation of LSR using $CO_2$ or Er:YAG lasers is that ablative laser resurfacing generally can not be performed on the patients with dark complexions. The removal of pigmented epidermis tissue can cause severe cosmetic disfigurement to patients with a dark complexion, which may last from several weeks up to years, which is considered by most patients and physicians to be unacceptable. Another limitation of LSR is that ablative resurfacing in areas other than the face generally have a greater risk of scarring. LSR procedures in areas other than the face result in an increased incidence of an unacceptable scar formation because the recovery from skin injury within these areas is not very effective.

In an attempt to overcome the problems associated with LSR procedures, a group of NCR techniques has emerged. These techniques are variously referred to in the art as non-ablative resurfacing, non-ablative subsurfacing, or non-ablative skin remodeling. NCR techniques generally utilize non-ablative lasers, flashlamps, or radio frequency current to damage dermal tissue while sparing damage to the epidermal tissue. The concept behind NCR techniques is that the thermal damage of only the dermal tissues is thought to induce wound healing which results in a biological repair and a formation of new dermal collagen. This type of wound healing can result in a decrease of photoaging related structural damage. Avoiding epidermal damage in NCR techniques decreases the severity and duration of treatment related side effects. In particular, post procedural oozing, crusting, pigmentary changes and incidence of infections due to prolonged loss of the epidermal barrier function can usually be avoided by using the NCR techniques.

Figure 2:
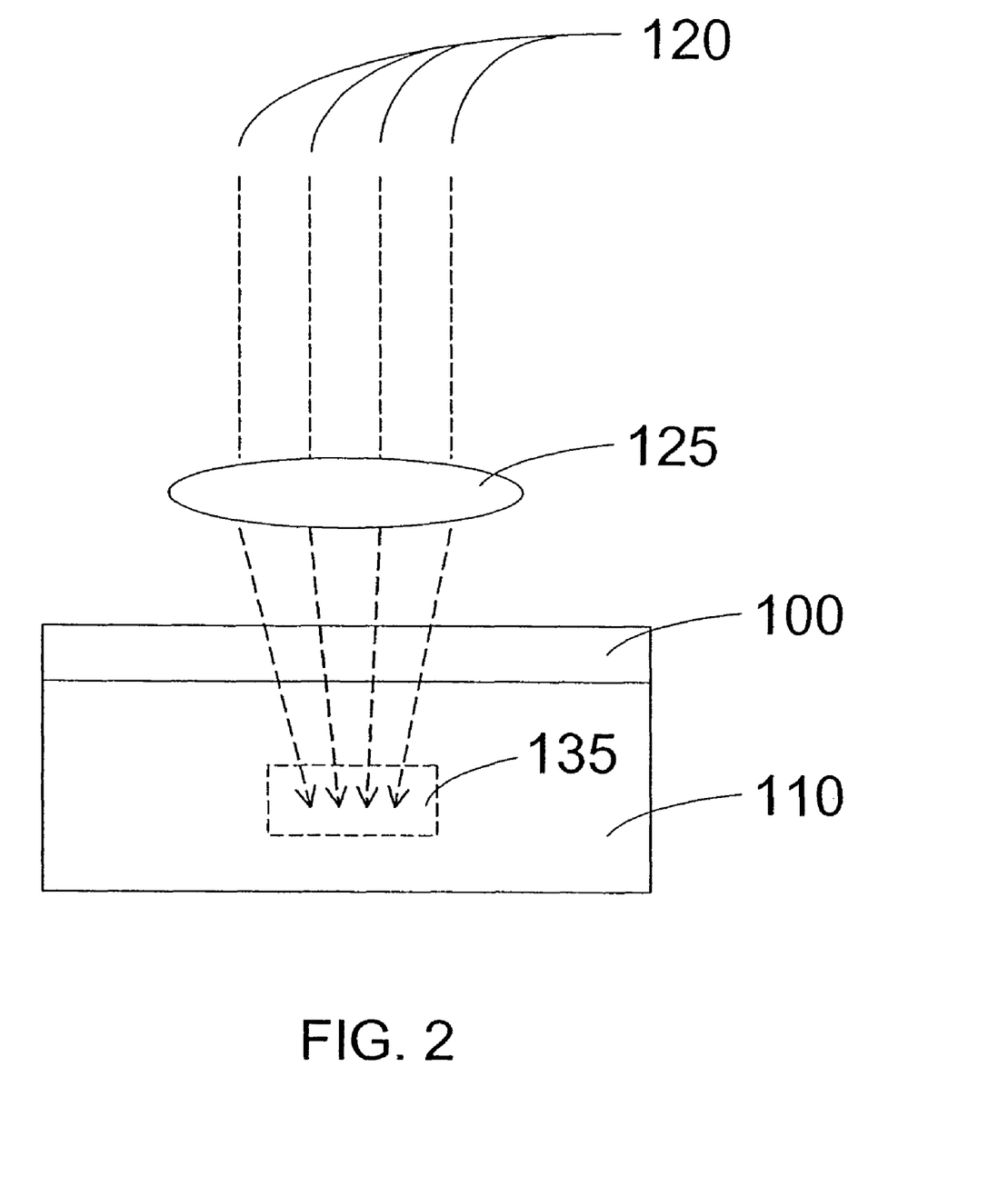
FIG. 2 is a schematic drawing of a cross section of a tissue treated using the NCR method.

In the NCR method of skin treatment, illustrated schematically in FIG. 2, selective portions of dermal tissue 135 within the dermal layer 110 are heated to induce wound healing without damaging the epidermis 100 above. Selective dermal damage that leaves the epidermis undamaged can be achieved by cooling the surface of the skin and focusing electromagnetic energy 120, which may be a laser beam, onto dermal region 135 using lens 125. Other strategies are also applied using nonablative lasers to achieve damage to the dermis while sparing the epidermis in NCR treatment methods. Nonablative lasers used in NCR procedures generally have a deeper dermal penetration depth as compared to ablative lasers used in LSR procedures. Wavelengths in the near infrared spectrum can be used. These wavelengths cause the nonablative laser to have a deeper penetration depth than the very superficially-absorbed ablative Er:YAG and $CO_2$ lasers. Examples of NCR techniques and apparatus are disclosed by Anderson et al. in U.S. Patent Publication No. 2002/0161357.

While it has been demonstrated that these NCR techniques can assist in avoiding epidermal damage, one of the major drawbacks of these techniques is their limited efficacies. The improvement of photoaged skin or scars after the treatment with NCR techniques is significantly smaller than the improvements found when LSR ablative techniques are utilized. Even after multiple treatments, the clinical improvement is often far below the patient's expectations. In addition, clinical improvement is usually several months delayed after a series of treatment procedures. NCR is moderately effective for wrinkle removal and is generally not effective for dyschromia. One advantage of NCR is that it does not have the undesirable side effects that are characteristic of the LSR treatment, such as the risk of scarring or infection.

Another limitation of NCR procedures relates to the breadth of acceptable treatment parameters for safe and effective treatment of dermatological disorders. The NCR procedures generally rely on an optimum coordination of laser energy and cooling parameters, which can result in an unwanted temperature profile within the skin leading to either no therapeutic effect or scar formation due to the overheating of a relatively large volume of the tissue.

A further problem of both ablative and nonablative resurfacing is that the role of keratinocytes in the wound healing response is not capitalized upon. Keratinocyte plays an active role in the wound healing response by releasing cytokines when the keratinocyte is damaged. During traditional ablative resurfacing procedures, the keratinocytes are removed from the skin along with the epidermis, thereby removing them from the healing process altogether. On the other hand, in traditional non-ablative procedures, the keratinocytes, which are located in the epidermis, are not damaged, and therefore do not release cytokines to aid in the healing process.

Citation or identification of any document in this application is not an admission that such document is available as prior art to the present invention.

SUMMARY OF THE INVENTION

In view of the above-mentioned disadvantages and limitations of LSR and NCR, there is an increasing demand for an effective and safe treatment that repairs or alleviates skin defects. In recognition of this demand, the present invention relates to improved methods and apparatus for treating skin. Methods and apparatus according to the present invention are safe, effective, and the various embodiments of the apparatus are relatively simple to manufacture and use.

In an embodiment according to the present invention, methods and apparatus for damaging dermal tissue in particular patterns ('micro-lines') to promote effective and fast wound healing are described. 'Damaging' is defined as inducing cell death in one or more regions of the dermal tissue of interest ('lethal damage'), or stimulating the release of cytokines, heat shock proteins, and other wound healing factors without stimulating necrotic cell death ('sublethal damage'). 'Micro-lines' are narrow regions of damaged dermal tissue, generally less than 1 mm in width, that extend from the surface of the skin into the epidermis and, optionally, through the epidermis and into the dermal layer. The micro-lines are long in one direction along the surface of the skin, generally at least four to five times as long as the width of the micro-lines, and may traverse part or all of the region of skin being treated.

In another embodiment according to the present invention, a method for damaging dermal tissue is provided wherein a plurality of micro-lines of damaged regions are created that extend from the skin surface into the epidermal tissue and, optionally, into the dermal tissue.

In another embodiment of this invention, several micro-lines of damaged regions of dermal tissue may be formed simultaneously. The micro-lines thus formed may be nearly parallel, and may be linear, curved, or wavy.

In another embodiment according to the present invention, the fractional coverage of the skin surface with micro-lines of damaged tissue in the region of skin being treated is preferably about 50%. In other embodiments according to the present invention, the fractional coverage of the skin by micro-lines can range from about 10% to about 80%. The fractional coverage can be controlled by varying the width of the individual micro-lines, by varying the spacing between adjacent micro-lines, or by varying both the width and spacing of the micro-lines. The fractional coverage may also be increased by creating more than one set of micro-lines over a given region of skin being treated.

In yet another embodiment according to the present invention, one or more sources of electromagnetic radiation ('EMR') such as a laser may be used to create the plurality of micro-lines.

In yet another embodiment according to the present invention, one or more diamond knives or scalpels or other mechanical implements may create the plurality of micro-lines.

In another embodiment of the invention, an apparatus for treating skin by creating micro-lines of damage is provided. The apparatus includes a damaging means for causing cell death in dermal tissue, and an optional control unit for controlling the damaging means, which may be used to create a plurality of micro-lines in the dermal tissue of interest.

In yet another embodiment according to the present invention, the apparatus comprises one or more optical energy sources such as a laser as damaging means to create the plurality of micro-lines.

In yet another embodiment according to the present invention, the apparatus comprises one or more diamond knives or scalpels or other mechanical implements as damaging means to create the plurality of micro-lines.

In yet another embodiment according to the present invention, the apparatus comprises a radio frequency (RF) device as damaging means to create the plurality of micro-lines.

In another embodiment of the invention, the apparatus comprises a housing containing the damaging means that is manually translated across a region of the skin to produce the micro-lines.

In another embodiment of the invention, the apparatus comprises a housing containing the damaging means and a scanning mechanism that automatically translates the damaging means across a region of the skin in a controlled manner to produce the micro-lines.

BRIEF DESCRIPTION OF THE DRAWINGS

The following detailed description, given by way of example, but not intended to limit the invention solely to the specific embodiments described, may best be understood in conjunction with the accompanying drawings, in which.

Throughout the drawings, the same reference numerals and characters, unless otherwise stated, are used to denote like features, elements, components, or portions of the illustrated embodiments. Moreover, while the present invention will now be described in detail with reference to the Figures, it is done so in connection with the illustrative embodiments and is not limited by the particular embodiments illustrated in the Figures.

DETAILED DESCRIPTION OF THE INVENTION

In accordance with one embodiment of the present invention, the epidermis, the dermis, or both the epidermis and dermis may be damaged in regions that are small in at least one dimension along the surface of the skin, where 'small' denotes a size less than about one mm, to achieve the desired effects of wound healing and tissue remodeling.

Figure 3:
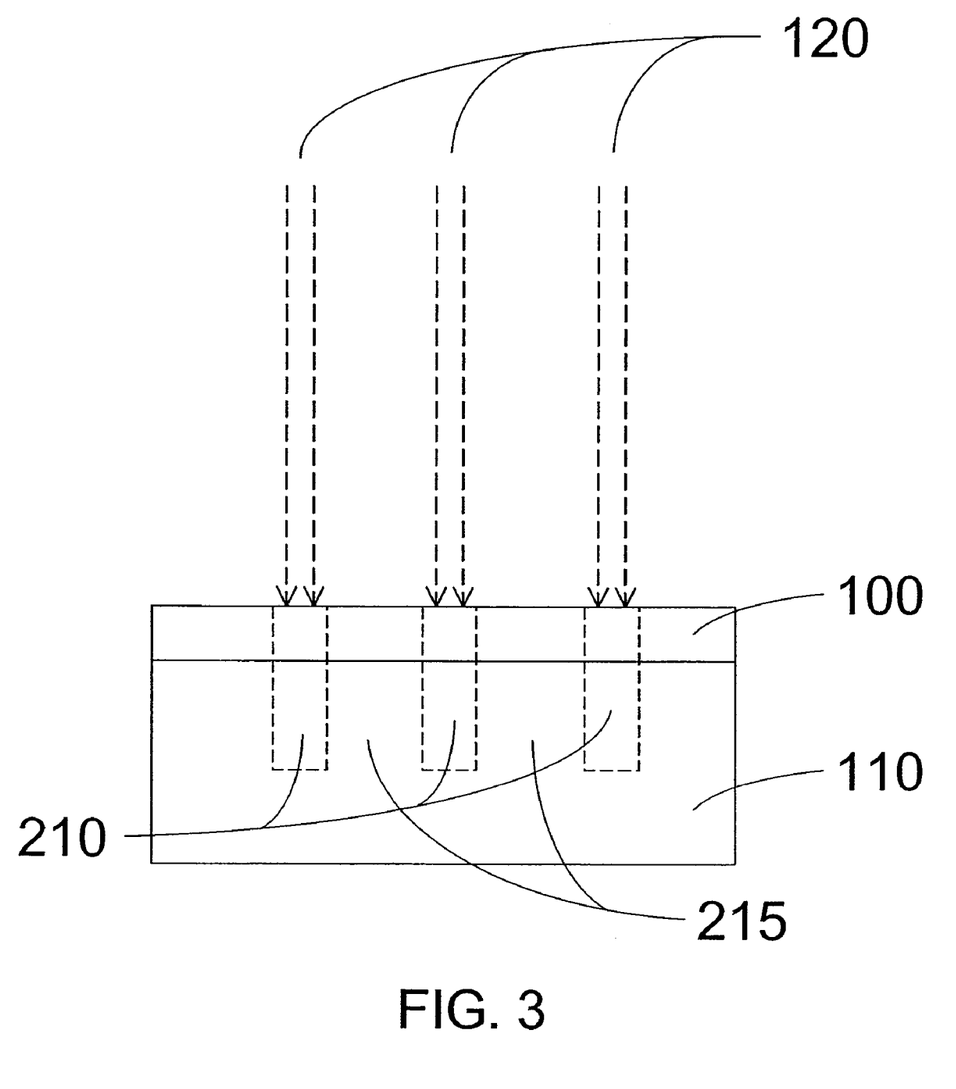
FIG. 3 is a schematic drawing of a cross section of a tissue treated in accordance with an embodiment of the present invention.

In one preferred embodiment of the invention, regions of damaged tissue are created in both the dermis and epidermis for reasons that will be described below. FIG. 3 depicts a cross section of dermal tissue comprising epidermal layer 100 and dermal layer 110, treated in accordance with a present embodiment of the invention. As shown in FIG. 3, regions of damaged tissue 210 are created in the epidermis and the dermis by beams of electromagnetic energy 120. In contrast to LSR and NDR, where the purpose is to achieve homogeneous damage at a particular depth within the skin (see FIGS. 1 and 2 respectively), in at least one embodiment of the present invention, the creation of micro-lines of damaged tissue extend through the epidermis but spare regions of undamaged tissue 215 surrounding each micro-line. The micro-lines of damaged tissue 210, each of which extends laterally for some distance parallel to the skin surface (corresponding to a direction into and/or out of the page for the cross-section shown in FIG. 3), together with the regions of undamaged tissue 215 between the micro-lines, form the basis for a macroscopic treatment effect.

Methods and apparatus according to the present invention can be used, for example, to reduce the appearance of wrinkles and lines, improve skin texture, rejuvenate the appearance of the skin, reduce skin pigmentation (either generally or in specific foci such as freckles, birthmarks, lentigos or tattoos), treat dyschromia, improve the appearance of scar tissue, treat acne, and treat vascular lesions such as port-wine stains, hemangiomas, telangiectasias, venous lakes, and spider and cherry angiomas. The range of dermatological conditions that can be treated according to the present invention includes virtually any type of dermatological defect in need of correction.

The methods and apparatus according to the present invention can be used to treat skin in any patient of any age. However, the present invention is particularly useful in the treatment of aged skin, in particular photoaged skin. Likewise, the present invention can be used to treat skin anywhere on the body and is particularly well suited for the treatment of facial skin such as, for example, the perioral and periocular skin.

In one embodiment, the methods according to the present invention can be carried out without analgesia or anesthesia. However, if desired, any suitable analgesic or anesthetic methods can be used. For example, the present methods can be performed following topical administration of lidocaine. Alternatively, or additionally, the methods of the invention can be performed with conductive or convective cooling of the surface region of the skin prior to and/or during creation of the micro-lines of damaged tissue. Such cooling can be applied to reduce or eliminate perceived pain or discomfort during the treatment. Cooling can also be applied to reduce or eliminate dermal tissue damage near or at the surface of the skin, including all or part of the epidermis.

Without being bound by theory, methods of the invention are understood to induce damage or "wounding" of dermal tissue, which in turn stimulates a "wound healing response" within the dermal tissue. The wound healing response in turn promotes tissue regeneration. The term "wound" as used herein refers to physically induced tissue damage, which may or may not involve necrotic cell death. Wound healing in the skin is a process involving, among other things, the release of cytokines, heat-shock proteins, and growth factors, followed by the stimulation of cellular migration, cellular proliferation, and extracellular matrix ("ECM") remodeling. For example, it is known from corneal model systems that injured epithelial cells stimulate fibroblast myodifferentiation through one or more soluble factors, including TGF-beta. This enhances stromal remodeling. (Nakamura, K. (2003) Cornea, 2(7 Suppl):S35-47). Furthermore, stimulation of myofibroblasts, which leads to delayed tissue contraction, can produce tissue tightening. Thus, controlled myodifferentiation and myofibroblast stimulation will allow delayed and effective wound contraction and therefore, desired tightening of dermal tissue. These wound healing processes, including the remodeling of the ECM proteins collagen and elastin, are believed to contribute to the mechanism for regeneration and a rejuvenated appearance of the skin. Thus, in one embodiment, the present invention minimizes the appearance of lines and wrinkles.

The selected pattern and instrumentation used in wounding can influence the end result and the choice and combination of selected means from the options disclosed in the various embodiments of the invention disclosed herein is well within the level of skill in the art. In one embodiment, the extent of differentiation and/or contraction of myofibroblasts is modulated by the pattern of wounding and can be further enhanced by simultaneous application of applied agents. Such agents can be, for example, either topically or systemically administered. In another embodiment, further beneficial effects can result from vertical extrusion of necrotic epidermal and dermal components induced by application according to the present invention. Following thermal damage, such debris gradually migrates towards the surface of the skin before being sloughed off. Thus, controlled removal of pigment, for example melanin, can be achieved by extrusion, optionally followed by administration of an appropriate fill factor (e.g., collagen).

The present invention provides an optimal balance between the negative and positive effects of induced wounding. In one embodiment, this is achieved by damaging only fraction of the total skin surface in the dermal tissue of interest. In particular, according to the methods of the present invention, the skin is damaged in micro-line patterns, wherein line-shaped regions of wounding that extend into the epidermis, and optionally into the dermis, are surrounded by non-wounded areas. As a result, the extent of the wound-healing response is controlled, and the aesthetically undesirable side effects of wounding, such as edema, oozing, crusting, and burning discomfort, are reduced or eliminated.

Additionally, the present invention can restrict wounding to a fraction of cells within the dermal tissue of interest, and therefore the rate of recovery and healing is not limited by the need to generate entire cell layers anew. Instead, the "spared" cells are able to migrate laterally into the wounded areas to provide functional compensation. In this way, recovery can be rapidly achieved (e.g., re-epithelization can occur in as little as 24 hours following treatment). The micro-lines of dermal tissue damage formed when practicing the present invention have at least one dimension that is small, which allows repopulation of the damaged region from surrounding undamaged tissue over a small migration length.

The damage-producing source parameters may also be adjusted to determine the depth of the damage in the skin. For example, in one embodiment the dermal tissue damage can be induced selectively in the outer epidermis. Importantly, it has been found that using the methods according to the present invention to induce damage in the most superficial layers of the epidermis (including the outermost stratum corneum), does not compromise the barrier function of the skin. This is most likely due to the fact that, as a consequence of the small wound dimensions, surface keratinocytes are able to migrate laterally and therefore functionally compensate for those cells that have been destroyed. There is some evidence (see above) that simultaneous epidermal and dermal damage is synergistic in promoting tissue remodeling and promotes myofibroblast differentiation. This is an improvement over existing methods, wherein the skin's barrier function is more severely compromised, increasing susceptibility to infection and dehydration, and slowing re-epithelization.

Although particular depth ranges of the skin can be targeted to generate a pattern of thermal wounding that does not damage the surface, as described above, it is preferred that the methods and apparatus according to the present invention are employed to induce a pattern of wounding affecting both the superficial epidermis and the deeper dermis. This is particularly useful in situations where treatment is directed toward targets that may be located at varying depths within the skin. For example, when treating vascular disorders, such as port-wine hemangiomas, the blood vessels to be treated may be present at varying depths within the dermis. The methods and apparatus according to the present invention can be used to create micro-lines that are spaced close enough along the surface and extend deep enough into the dermal tissue such that they will damage all of the blood vessels in the dermal tissue of interest to more effectively treat this disorder.

An advantage of the present invention over treatment methods that require selective cooling of the surface to reduce or eliminate damage to the outer surface of the epidermis is that the present method allows for a simpler apparatus that does not require a cooling function. Cooling of the skin surface may optionally be used with various embodiments of the invention disclosed herein to reduce the amount of pain perceived by the person being treated. No surface cooling of the skin is required in some embodiments of the present method and apparatus to achieve the desired wounding patterns. Thus, a further advantage of the present invention is that the operational parameters of the apparatus (such as transverse velocity and power intensity, if any, of the damaging means) can be varied over a wider range during a treatment procedure. Operating conditions, including characteristics of the applied electromagnetic energy or blades, application of cooling or analgesics for pain control, and the like, are not constrained by restrictive balancing requirements between local heating and cooling effects.

Unlike methods that target a specific range of tissue depths, for example, by focusing of energy and/or selective superficial cooling, some embodiments according to the present invention are directed toward creating micro-lines of damaged tissue extending from the skin surface through the epidermis and dermis using directed energy sources. The resulting damaged regions extend over a broader range of tissue depths within the skin, and creation of these micro-lines is less sensitive to the specific location of the energy sources relative to the skin surface than when using methods that focus damage on specific depths within the dermal tissue. In these embodiments, the directed energy sources need not even contact the surface of the skin to create the desired micro-lines of damaged tissue.

In an embodiment of the present invention, the average energy of each beam of electromagnetic radiation is approximately 0.1-10W. The energy of each beam may also be chosen preferentially in the range of approximately 0.5-3W, or more preferentially approximately 1 W. The energy chosen for a given application depends on the wavelength of energy used, the tissue being treated, and the desired depth of the micro-lines. Average beam energies can be selected outside of the ranges listed above depending on the type of thermal wound characteristics desired.

An advantage of some embodiments according to the present invention is that the micro-line wounding patterns extend over a range of depths within the skin, producing a -wound healing effect that is enhanced over that which can be achieved by targeting only a single tissue layer. Producing a continuous micro-line pathway of damage extending from the skin surface down through the epidermis and into the dermis can facilitate the vertical extrusion of necrotic debris, giving rise to beneficial effects including controlled pigment removal.

In one embodiment of the present invention, the micro-lines of damaged tissue may have a depth in a direction normal to the surface of the skin of up to about 1000 μm. In another embodiment, the depth of the micro-lines is up to about 300 μm. If the tissue damage is to be limited primarily to the epidermis, then the depth of the micro-lines may be limited to about 50-100 μm. The depth of the damaged regions may be selected to be any distance less than or about equal to the maximum depth noted, and selection of a particular depth for a given application will depend on the type of results to be achieved by stimulation of wound healing. When treating a single region of skin, the plurality of micro-lines created may have different depths. Further, the depth of a single micro-line may vary along its length. This may be done to target specific areas within the skin for damage and subsequent healing, or to reduce the density of damage created at deeper levels in the skin.

The width of the micro-lines as measured in a direction parallel to the surface of the skin may be between about 10 μm and 1 mm, although it may be preferable to create micro-lines having a width of approximately 30 and 400 μm. It may be even more preferable to create micro-lines having a width of approximately 60 and 120 μm, and it may be most preferable to create micro-lines having a width of approximately 80 μm.

It is preferable for micro-lines of damaged tissue that are created in the dermal tissue to have sufficient undamaged tissue adjacent to them over at least most of their length to promote rapid healing and other beneficial effects, including those as described above. In one embodiment according to the present invention, the average width of the undamaged regions of skin between adjacent micro-lines may be approximately the same as the width of the micro-lines, corresponding to a fractional coverage of the skin with damaged regions of about 50%. In other embodiments according to the present invention, the average width of the undamaged regions of skin between the micro-lines may be as large as approximately two, three, four, or nine times the average width of the adjacent micro-lines, corresponding to fractional coverage of the skin by damaged regions of about 33%, 25%, 20%, and 10%, respectively. In other embodiments according to the present invention, the average width of the undamaged regions of skin between the micro-lines may be as small as approximately two-thirds, one-half, or one-fourth of the average width of the adjacent micro-lines, corresponding to fractional coverage of the skin by damaged regions of about 60%, 67%, and 80%, respectively. The fractional coverage of the skin by damaged regions in other embodiments according to the present invention may include any values lying between the specific ratios of about 10% to 80% noted above. The micro-lines should also be spaced close enough together to provide sufficient density of damaged tissue in the treated area to obtain the desired results.

A variety of micro-line patterns of damaged tissue regions may be created in the dermal tissue of interest while keeping in spirit with the embodiments according to the present invention. Examples of such patterns are shown in, but not limited to, FIGS. 4(a)-4(i). In these figures, the width of the micro-lines 210 is approximately the same as the width of the regions of undamaged tissue 215 between them. The ratio of the width of these regions can be varied to achieve the fractional surface coverage of the skin by micro-lines desired.

Figure 4A:
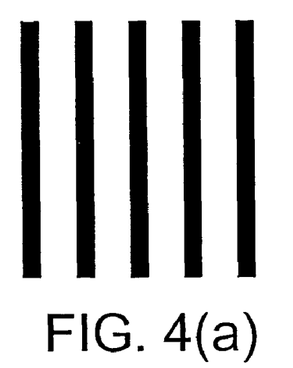
FIGS. 4(a)-4(i) depict various patterns of micro-lines in accordance with an embodiment according to the present invention.
Figure 4B:
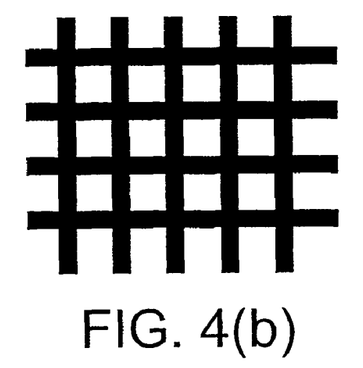
Figure 4C:
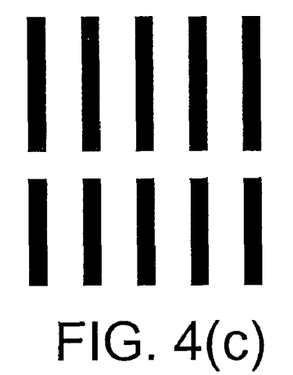
Figure 4D:
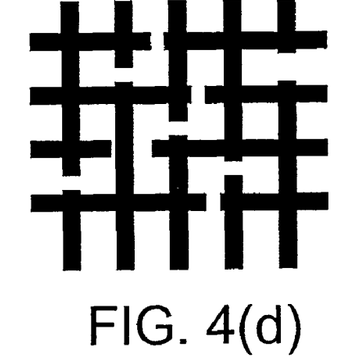
Figure 4E:
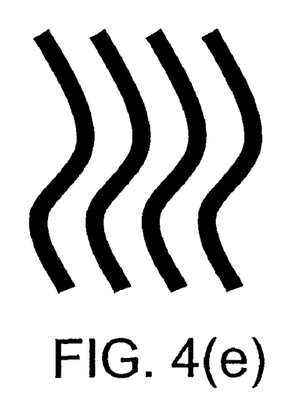
Figure 4F:
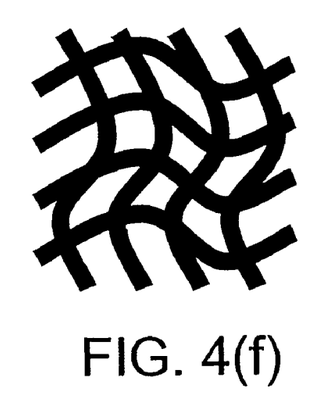
Figure 4G:
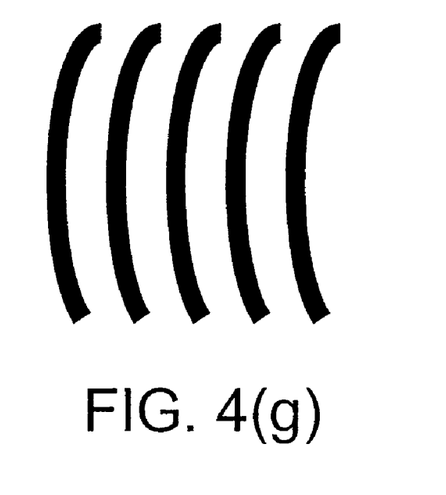
Figure 4H:
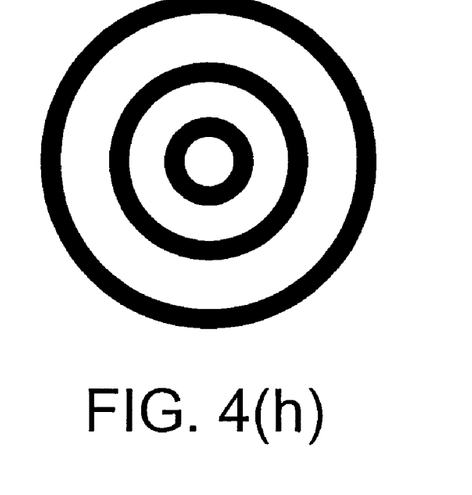
Figure 4I:
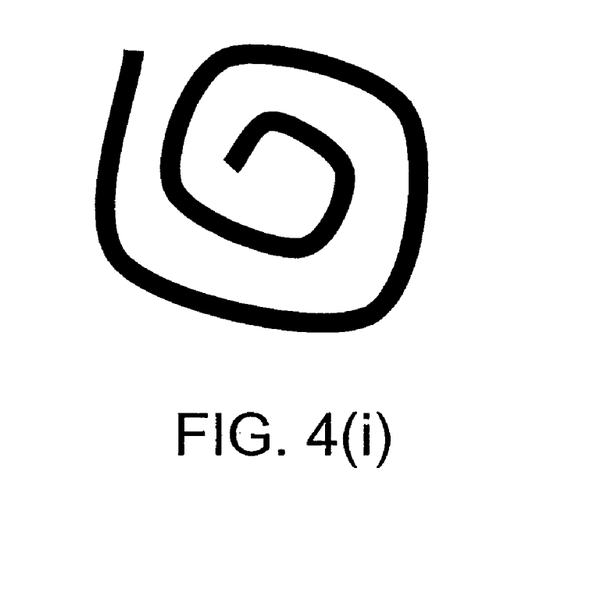

In one embodiment according to the present invention, a number of essentially parallel micro-lines of damaged tissue 210 may be created as shown in FIG. 4(a). Alternatively, a cross pattern of micro-lines 210 may be created as shown in FIG. 4(b). Such cross patterns will have a larger fractional coverage for a given spacing and width of micro-lines than a non-crossed pattern. Such cross patterns of micro-lines can also be made at any relative angle in addition to the nearly-perpendicular sets of micro-lines shown in FIG. 4(b). In other embodiments, one or more micro-lines 210 may be discontinuous as shown in FIG. 4(c), and FIG. 4(d). These discontinuous micro-lines can be considered as comprising a series of shorter micro-lines. In addition to straight micro-lines, many other patterns may be created. It is within the scope of this invention to create one or more wavy micro-lines 210 as shown in FIGS. 4(e) and 4(f). Optionally, curved micro-lines 210 may be created as shown in FIG. 4(g). Such curved lines may be shaped to follow certain contours of the skin being treated or contours of defects in the skin. Other geometric patterns of micro-lines may also be used. For instance, micro-lines 210 having the form of concentric circles may be created, as shown in FIG. 4(h). Alternatively, micro-lines 210 having the shape of a spiral may be formed as shown in FIG. 4(i). Any of the micro-line patterns shown in FIGS. 4(e)-(i) may also be formed in a discontinuous pattern similar to that shown in FIG. 4(c).

The length of the micro-lines is preferably at least four to five times the width of the micro-lines at the surface of the skin. The length-to-width ratio of a micro-line may be much larger, with no defined upper limit, and individual micro-lines may traverse the entire region of skin being treated. Some micro-line patterns such as the concentric circles in FIG. 4(h) will not have a clearly defined length-to-width ratio, but nevertheless fall within the scope of the present invention. The anisotropic nature of the micro-line patterns can yield desirable healing results that cannot be achieved with more isotropic or homogeneous patterns such as a distribution of dot-shaped regions of damaged tissue. Micro-line patterns of damage can result in tissue shrinkage and wound healing reactions that vary in the directions parallel to and orthogonal to the micro-lines. It thus is possible to obtain desirable treatment results, for example, by creating a series of micro-lines that are parallel to a set of elongated features such as wrinkles in the skin. Alternatively, optimal treatment results may be obtained in some cases by creating micro-lines that are parallel to elongated features present in the skin. Formation of micro-lines of damaged dermal tissue allows for easier and more uniform application of wound patterns over larger areas of skin than that obtainable by using other patterns.

Figure 5:
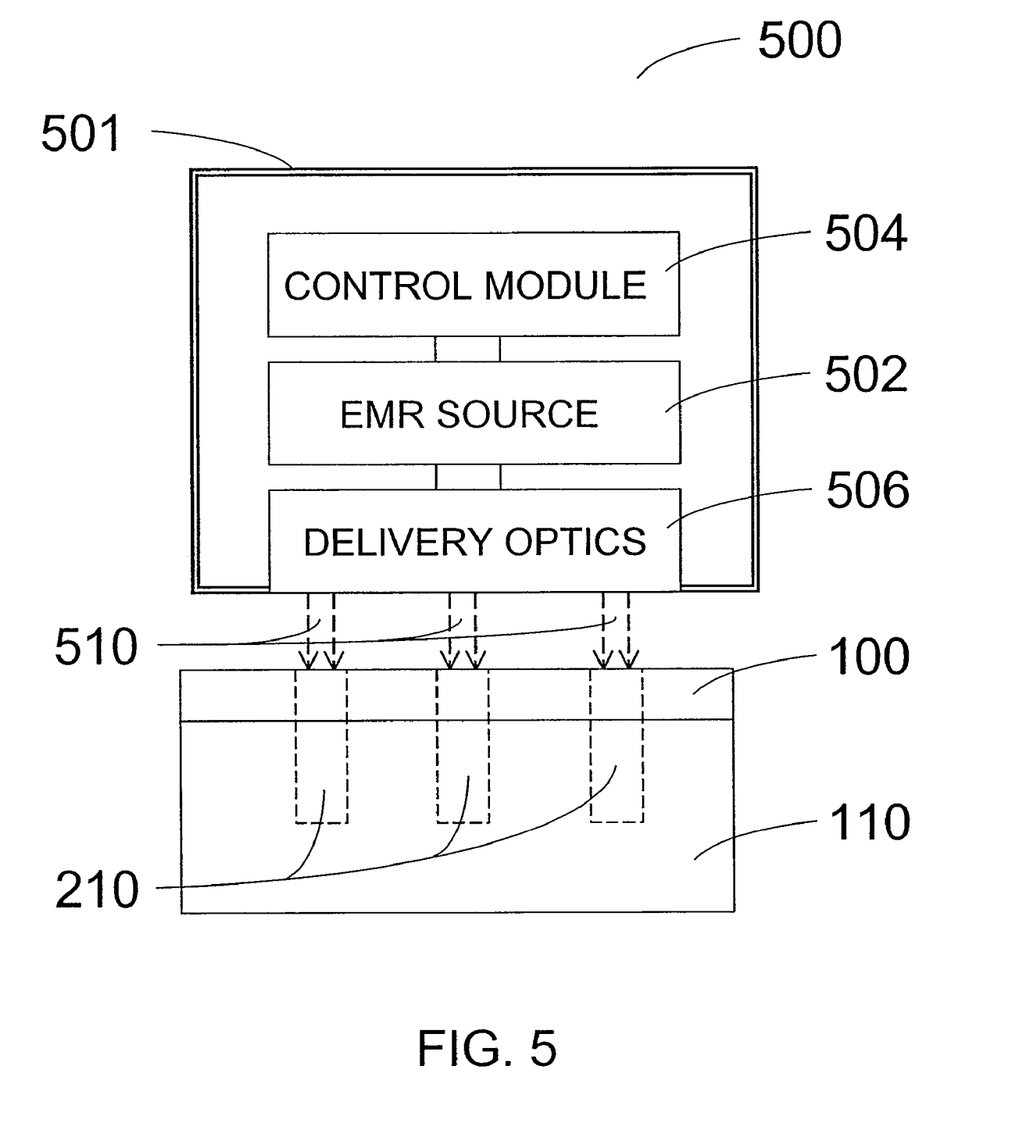
FIG. 5 is a schematic illustration of an apparatus for conducting dermatological treatments using electromagnetic energy according to one embodiment of the present invention.

In one embodiment of the present invention, the micro-lines of damaged tissue may be created by directing a plurality of beams of electromagnetic radiation ('EMR') onto the skin. FIG. 5 illustrates a progressive use of a first exemplary embodiment of a fractional resurfacing apparatus 500 for conducting various dermatological treatments using EMR and generating a pattern of micro-lines of skin damage over a target region of skin according to the present invention. The system 500 may be used for collagen remodeling, removal of unwanted pigment or tattoo, and other dermatological applications. As shown in FIG. 5, the apparatus 500 comprises a case 501, an EMR source 502, a control module 504, and delivery optics 506. The EMR source 502, control module 504, and delivery optics 506 are configured to direct a plurality of discrete beams of electromagnetic radiation 510 towards the epidermis 100. In one embodiment according to the present invention, housing 501 is translated over a region of the skin being treated. This motion of the housing 501 and of the delivery optics 506 contained at least partially therein to create micro-lines of damage 210 in the skin. Preferably, the velocity of the beams of electromagnetic radiation over the tissue being treated is approximately 0.5-10 cm/sec, and most preferably about 1-2 cm/sec.

In one exemplary variant according to the present invention, the control module 504 can be in wireless communication with the EMR source 502. In another variant, the control module 504 may be in wired communication with the EMR source 502. In another exemplary variant according to the present invention, the control module 502 can be located outside of the case 501. In another variant, the EMR source 502 is located outside of the case 501. In still another variant, both the control module 504 and the EMR source 502 are located outside of the case 501.

The radiation produced by the EMR source 502 can be optical radiation that is collimated or which may slightly focused, and directed by the delivery optics 506. In one embodiment according to the present invention, the EMR source 502 may comprise, but is not limited to, a diode laser, a diode-pumped solid state laser, an Er:YAG laser, a Nd:YAG laser, an argon-ion laser, a He—Ne laser, a carbon dioxide laser, an eximer laser, or a ruby laser. The beams of radiation produced by the EMR source and directed by the delivery optics may optionally be continuous or pulsed.

In another embodiment of the present invention, each beam 510 has an average energy delivery rate of approximately 1 W and may operate in different wavelengths depending on the application and treatment effect desired. For example, to remove wrinkles it may be preferable to have a laser with a wavelength in the approximate range of 1000-2300 nm. For pigment removal, it may be preferable to have a laser with a wavelength in the approximate range of 400-1000 nm. Water-absorbed wavelengths in the range of 1200-2300 nm may also be used for controlled pigment removal, and it may be preferable in some treatments to employ a wavelength of up to approximately 3000 nm. In contrast to treatment concepts that rely on a homogeneous electromagnetic radiation (EMR) field delivery, such as conventional selective photothermolysis, the amount of pigment removed by employing the present invention is controlled primarily by the density and depth of the micro-lines rather than by the dosimetry of the beam. Each beam of electromagnetic energy delivered by the delivery optics 506 may be collimated or, alternatively, slightly focused.

The control module 504 provides application specific settings to the EMR source 502. The EMR source 502 receives these settings, and generates EMR based on these settings. The settings can control, inter alia, the wavelength and frequency, and the beam profile of the EMR. If the EMR source 502 is pulsed, the control module 504 can also control the pulse duration for each EMR pulse, the fluence of the EMR, the number of EMR pulses, and/or the delay between individual EMR pulses. The control module 504 may be any sort of data processing apparatus that receives, processes, and outputs signals, such as a personal computer, a microprocessor, a microelectronic assembly, or a specially designed control unit.

A preferred exposure time of a local region of skin to radiation delivered by the delivery optics 506 is approximately 1 to 50 ms. The exposure time is determined by the diameter of each beam of energy 510, and by the velocity of beam in a direction parallel to the surface of the skin. If the EMR source is pulsed, the local exposure time is also determined by the pulse rate and duration of the individual pulses. The local exposure time corresponds to the total time required for a beam of energy delivered by the delivery optics 506 to pass over a particular location on the skin. If the exposure time is less than 1 ms there may not be enough local thermal damage to induce wound healing. Exposure times greater than 50 ms may lead to excessive local thermal damage and to negative side effects.

Delivery optics 506 are configured to direct electromagnetic radiation generated by EMR source 502 towards the surface of the skin in the form of a plurality of beams 510. In an embodiment according to the present invention, delivery optics 506 comprises one or more fiber optic guide or other form of waveguide. In other embodiments, delivery optics 506 may further comprise one or more beam splitters, including but not limited to prisms or partially-reflecting mirrors. In variants according to the present invention wherein the EMR source 502 is located outside of the case 501, delivery optics 506, which guide the EMR into the housing 501 and directs it towards the skin, maybe located partially outside of housing 501. In one such variant, the delivery optics comprises one or more lengths of flexible optical fiber that originate at EMR source 502 and terminate within housing 501. In this variant, delivery optics 506 may further comprise one or more beam splitters located within housing 501, and delivery optics 506 are configured to direct a plurality of beams 510 towards the skin.

In an exemplary embodiment according to the present invention, the fractional resurfacing apparatus 500 may optionally include a position sensor, which is in communication with the control module 504. The position sensor is capable of determining the relative velocity between the surface of the skin and the fractional resurfacing apparatus containing the delivery optics 506. The position sensor can be an optical mouse, one or more wheels, a track ball, a conventional mouse, and the like.

A position sensor can be used as a safety control to optimize the characteristics of the micro-lines formed in practicing the present invention, and also to protect the skin from overexposure to EMR. If the measured velocity of the apparatus along the skin is less than a predetermined velocity, then local exposure times to the energy sources may exceed 50 ms and have a negative impact on the tissue. For example, lateral heat diffusion may result in the transition from a fractional wounding pattern to a contiguous wounding pattern, leading to pronounced side effects including potential scarring.

In one embodiment according to the present invention, the control unit compares the velocity measured by the position sensor with a predetermined velocity during treatment of the skin. If the measured velocity is lower than a predetermined cut-off velocity, then the EMR source 502 is turned off or the EMR delivered by the delivery optics is otherwise interrupted.

In an alternative embodiment, the position sensor may be used in conjunction with the control module 504 to vary the intensity of the EMR provided by the EMR source 502 during treatment of the skin. The intensity of the radiation directed onto the skin by delivery optics 501 may be adjusted to be approximately proportional to the velocity measured by the position sensor, which would result in a more uniform energy density being applied to create each micro-line as the translational velocity of the apparatus 500 over the skin varies.

If the EMR source 502 provides a pulsed source of radiation to delivery optics 506, then control module 504 can be configured to vary the duration and/or frequency of the pulses based on the velocity measured by the position sensor. This represents an alternative method that may be employed to provide better control of the characteristics of the micro-lines formed when practicing embodiments of the invention. Other control methods may be employed in ways known to those skilled in the art and in accordance with the present invention to control the characteristics of the micro-lines by using a position sensor in conjunction with the EMR source 502 and control module 504.

In practicing methods according to the present invention, a range of EMR parameters can be used depending on the desired effects. In one embodiment, EMR parameters may be adjusted such that the temperature of the tissue damaged in the micro-lines is raised sufficiently to stimulate the release of cytokines, heat shock proteins, and other wound healing factors, without stimulating necrotic cell death. In another and preferred embodiment, the EMR parameters are adjusted such that necrotic cell death is induced in the damaged regions of dermal tissue.

In an exemplary embodiment according to the present invention, the case 501 of apparatus 500 shown in FIG. 5 may have a handle attached to it. In this variant, apparatus 500 may be manually translated over the skin such that beams of radiation 510 produce micro-lines of damage in a desired pattern.

In an alternative embodiment of the present invention, apparatus 500 further comprises scanning means capable of directing the beams of electromagnetic energy in a path along the skin being treated while the housing 501 is held essentially stationary with respect to a region of the skin to be treated. The scanning means may comprise a structure such as a platform, or plate that is movably attached to housing 501, and a moving means such as a motor. At least a part of the delivery optics 506 may be mounted to the structure. Alternatively, the scanning means may comprise one or more mirrors configured to reflect the beams of radiation, and a moving means for controllably adjusting the positions and/or angles of the mirrors. In these embodiments, control module 504 or other control means may be employed in conjunction with the scanning means to controllably scan a plurality of beams of radiation 510 across the surface of the skin to create micro-lines of a desired pattern. Mechanisms and control methods for performing this beam scanning function may be chosen from among those known to persons of skill in the art.

In another embodiment of the invention, the micro-line regions of damaged dermal tissue may be created mechanically using a number of diamond knives, microblades, scalpels, or similar cutting means (hereinafter "blades"). Apparatus 600, shown schematically in FIG. 6, may be used to create a pattern of micro-lines of tissue damage in accordance with an embodiment of the present invention. Apparatus 600 comprises a plurality of blades 610 mounted to base 620. Blades 610 are mounted at intervals along an axis such that they are uniformly or non-uniformly spaced. The spacing of blades 610 corresponds to the spacing of the micro-lines that can be created using this apparatus. The width of the micro-lines created by this apparatus is determined by the width of the blades 610. The blade width may be the same for all blades 610, or alternatively one or more blades may have different widths. Apparatus 600 may optionally comprise handle 630.

Figure 6:
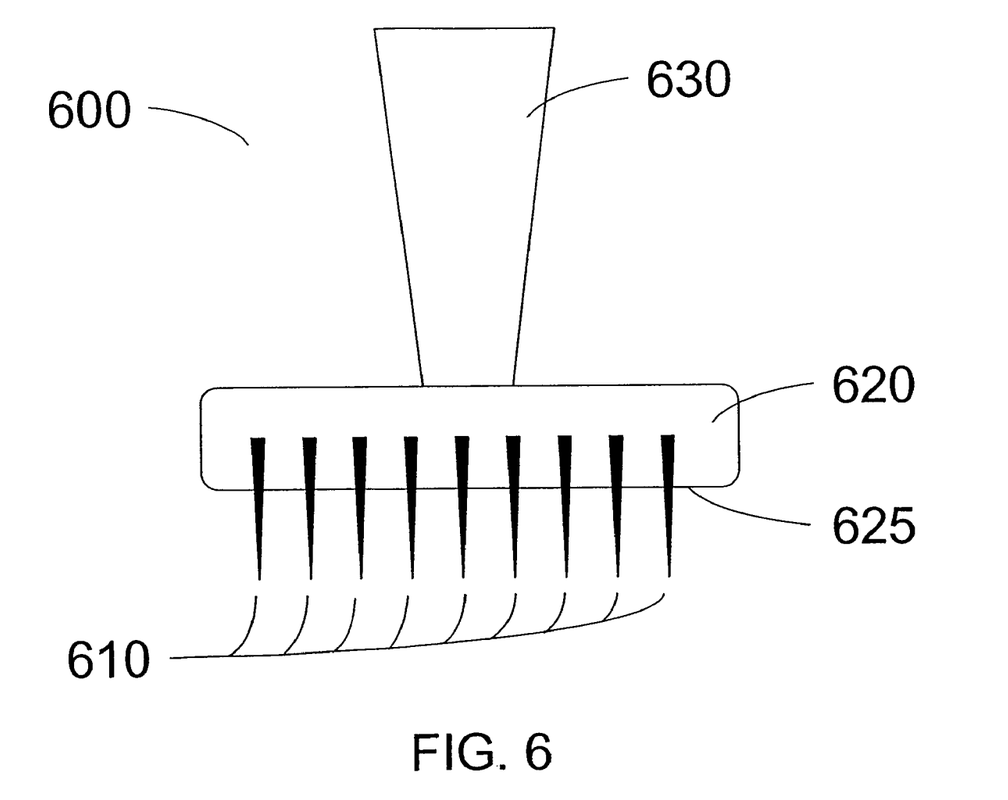
FIG. 6 is a schematic illustration of an apparatus for conducting dermatological treatment using mechanical means according to one embodiment of the present invention.

In this embodiment, apparatus 600 is pressed onto the skin such that the exposed portions of blades 610 penetrate the skin and the lower surface 625 of base 620 contacts the surface of the skin. Apparatus 600 can be manually translated along the region of skin being treated, and blades 610 will form a set of parallel micro-lines in the skin.

The distance that blades 610 protrude from the lower surface 625 of base 620 can determine the depth of the micro-lines formed in accordance with this embodiment of the invention. This distance may be the same for all blades 610, or alternatively one or more blades may protrude different distances from lower surface 625. In another variant, apparatus 600 may also include adjusting means by which the spacing between blades and/or distance by which the exposed portions of blades 610 protrude from surface 625 can be adjusted.

The plurality of blades 610 may also be mounted to a mechanical device movably attached to a frame, and provided with moving means configured to move the device and blades over the area of tissue to be treated. A controller may optionally be employed with such a mechanical device, wherein the controller directs the movement of the blades. Such a controller may be any sort of data processing apparatus that receives, processes, and outputs signals, such as a personal computer, a microprocessor, or a specially designed control unit. The controller may optionally be integrated with the mechanical device apparatus.

In an embodiment according to the present invention, the blades create micro-lines that mechanically damage the epidermis and, optionally, the dermis. Preferably, the blades damage the tissue up to a depth of no more than 1000 μm from the outer surface of the skin, so that there would not be complete separation of the dermis. The blades are moved in a direction along the skin so that they create micro-lines of tissue damage in the skin. The width of the micro-lines may be up to 200 μm. It may be preferable to create micro-lines having a width of approximately 100 μm.

In another embodiment of the invention, the damaging means according to the present invention may be an apparatus comprising one or more blades mounted on a mounting surface, wherein the cutting edges of the blades protrude a defined distance from the lower face of the mounting surface and the cutting edges form a micro-line pattern in a plane parallel to the plane of the mounting surface. This apparatus may be employed to create micro-lines in the skin by a stamping technique, whereby the mounting surface is pressed against the region of skin being treated until the mounting surface contacts the skin surface and then removed. In this manner, micro-lines of damaged tissue can be created mechanically, wherein the depth of the damaged region is approximately equal to the defined distance that the cutting edges of the blades protrude from the mounting surface, and the pattern and length of the micro-lines formed by each stamping operation is set by the shape of the cutting edges of the blades. The mounting surface may be applied to the dermal tissue of interest manually, wherein the mounting surface may be attached to a handle or some other holding means. Alternatively, the mounting surface may be attached to a mechanical device capable of positioning the mounting surface relative to the dermal tissue of interest and pressing it against the skin.

In any of the mechanical means employing blades described above, the blades and the surface they are attached to may be cooled prior to applying the blades to the skin. This cooling may alleviate any pain felt by the subject of the treatment. The region of skin being treated may also be cooled before the blades are positioned to penetrate the skin. In another variant, a topical analgesic may be applied.

Fractional resurfacing may cause portions of the epidermis to be thermally damaged or ablated, thereby reducing the efficacy of the barrier function of the epidermis and in particular decreasing the stratum corneum. This facilitates the delivery of drugs or specific substances to the dermis and epidermis, which can either enhance the effects of the treatment, or decrease the side effects caused by partial damage of the epidermis and/or dermis. Groups of drugs and substances, which may enhance the efficacy of skin remodeling include growth factors, collagen byproducts, collagen precursors, hyaluronic acid, vitamins, antioxidants, amino acids and supplemental minerals among others. Groups of drugs and substances, which may decrease side effects, can be steroidal anti-inflammatory drugs, non-steroidal anti-inflammatory drugs, antioxidants, antibiotics, antiviral drugs, antiyeast drugs and antifungal drugs. In an exemplary embodiment of the present invention, the vitamins that are used may be vitamin C and/or vitamin E. The supplemental minerals used are copper and zinc. The antioxidants can be vitamin C and/or vitamin E.

Other embodiments of the present invention include methods of applying or gluing a specific disposable mask (a thin layer of material that may be continuous or discontinuous) to a region of the skin before creating micro-lines of damaged tissue. The optional use of such a mask may achieve several purposes. Individually embedded wires or mechanically enforced structures within the mask may be used to guide the damaging means and to ensure that the desired micro-line pattern is provided. A superficial guidance system incorporated in the mask may also be implemented to guide the treatment process. Also, the mask or layer may incorporate markers embedded in a spatial pattern that helps to determine the scanning velocity and the positioning of the damaging means.

Application of a mask in accordance with the present invention may also improve mechanical stability of the tissue (by acting as a wound dressing) after formation of the micro-lines. The mask may be also medially compounded or provided with embedded microchambers in order to release desired materials (e.g. analgesics, wound healing promoters, antibiotics or other modulators) into the tissue during or before the wounding process. The mask may comprise a polymer having a specific memory of contraction that may be activated by the treatment or which applies a continuous (directed) tension after wounding to direct the wound healing and remodeling process.

Several designs of a mask that provides "immediately sealing wound dressing" can be implemented in accordance with the present invention. In one embodiment, an apparatus having a plurality of blades is employed to mechanically produce micro-lines of damage. The blades cut through a thin mask which is glued to or otherwise attached to the skin, and immediately after this cutting a fast hardening glue is sprayed to the surface. Alternatively a tape having adhesive or adhering qualities may be rolled over the thin mask immediately after cutting. This tape may shrink in a well-defined way after coming into contact with the thin mask that is attached to the skin to help close the cut micro-lines and promote healing.

The invention is further described by the following numbered paragraphs:

1. A method for treating skin, said method including:
providing a skin damaging means;
applying said damaging means to create a plurality of micro-lines of damaged tissue in a region of skin separated by regions of undamaged skin tissue, wherein said micro-lines are substantially parallel and traverse at least part of said region of skin being treated.

2. The method of paragraph 1, wherein said damaging means comprises one or more beams of electromagnetic radiation.

3. The method of paragraph 1 or 2, wherein the source of said electromagnetic radiation comprises a laser, a diode laser, a ER:YaG laser, a Nd:YaG laser, an argon-ion laser, a He—Ne laser, a carbon dioxide laser, an eximer laser, or a ruby laser.

4. The method of any one of paragraphs 1 to 3, wherein the source of said electromagnetic radiation further comprises a beam splitter.

5. The method of any one of paragraphs 2 to 4, wherein the wavelength of the electromagnetic radiation is between approximately 400 nm and 1000 nm, or between approximately 1200 nm and 2300 nm.

6. The method of any one of paragraphs 2 to 5, wherein the average energy of each beam of electromagnetic radiation is approximately 0.1-10W, approximately 0.5-3W, or approximately 1 W.

7. The method of any one of paragraphs 1 to 6, wherein said damaging means comprises a plurality of blades, scalpels, diamond knives, or other cutting means.

8. The method of any one of paragraphs 1 to 7, wherein said micro-lines of damaged tissue extend into the skin to a depth of up to 50-1000 µm.

9. The method of any one of paragraphs 1 to 8, wherein the width of said micro-lines of damaged tissue at the skin surface is between about 10 µm and 1 mm, between about 30 µm and 400 µm, between about 60 µm and 120 µm, or approximately 80 µm.

10. The method of any one of paragraphs 1 to 9, wherein the width of undamaged skin tissue between adjacent micro-lines at the skin surface is approximately equal to the width of the adjacent micro-lines.

11. The method of any one of paragraphs 1 to 10, wherein the width of undamaged skin tissue between adjacent micro-lines is between about 10 µm and 1 mm, between about 30 µm and 400 µm, between about 60 µm and 120 µm, or approximately 80 µm.

12. The method of any one of paragraphs 1 to 11, wherein the width of undamaged skin tissue between adjacent micro-lines at the skin surface is approximately equal to twice the width of the adjacent micro-lines.

13. The method of any one of paragraphs 1 to 12, wherein the width of undamaged skin tissue between adjacent micro-lines is between about 20 µm and 2 mm, between about 60 µm and 800 µm, between about 120 µm and 240 µm, or approximately 160 µm.

14. The method of any one of paragraphs 1 to 13 wherein the micro-lines form a trace on the surface of the skin being treated that is a set of essentially parallel straight lines, essentially parallel curved lines, or essentially parallel wavy lines.

15. The method of any one of paragraphs 1 to 14 wherein at least a portion of the surface of said region of skin is superficially cooled before creation of said micro-lines and, optionally, cooled during creation of said micro-lines.

16. The method of paragraph 15 wherein at least a portion of said region of skin is superficially cooled by conductive or convective means.

17. An apparatus for treating skin, comprising:
a housing;
one or more sources of electromagnetic radiation;
an optical delivery system located at least partially within said housing, configured to direct a plurality of beams of said electromagnetic radiation onto the skin being treated to create a plurality of micro-lines of damaged tissue that traverse a region of skin being treated; and
a control module capable of controlling the characteristics of the electromagnetic radiation generated by said source of electromagnetic radiation.

18. The apparatus of paragraph 17 wherein said source of electromagnetic radiation comprises one or more of a laser, a diode laser, a ER:YaG laser, a Nd:YaG laser, an argon-ion laser, a He—Ne laser, a carbon dioxide laser, an eximer laser, or a ruby laser 19. The apparatus of paragraph 17 or 18 wherein said beams of electromagnetic radiation are pulsed.

20. The apparatus of any one of paragraphs 17 to 19 wherein said optical delivery system further comprises a beam splitter.

21. The apparatus of any one of paragraphs 17 to 20, wherein the wavelength of the electromagnetic radiation is between approximately 400 nm and 1000 nm, or between approximately 1200 nm and 2300 nm.

22. The apparatus of any one of paragraphs 17 to 21, wherein said beams of electromagnetic radiation are collimated or slightly focused.

23. The apparatus of paragraph 22, wherein the diameter of said beams of electromagnetic radiation at the surface of the region of skin being treated is between about 10 µm and 1 mm, between about 30 µm and 400 µm, between about 60 µm and 120 µm, or approximately 80 µm.

24. The apparatus of any one of paragraphs 17 to 23, wherein the average energy of each of said beams of electromagnetic radiation is approximately 1 W.

25. The apparatus of any one of paragraphs 17 to 24 further comprising a position sensor capable of detecting the velocity of said beams of electromagnetic radiation along the skin, and wherein said position sensor is configured to provide signals to said control module.

26. The apparatus of paragraph 25, wherein said control module is configured to shut off said source of electromagnetic radiation or otherwise interrupt said beams of electromagnetic radiation when the velocity of said beams across the surface of said region of skin falls below a predetermined value.

27. The apparatus of paragraph 25 or 26, wherein said control module, position sensor, and source of electromagnetic radiation are configured to vary the intensity of said beams of electromagnetic radiation in proportion to the velocity at which said beams traverse the surface of said region of skin.

28. The apparatus of any one of paragraphs 25 to 27, wherein said beams of electromagnetic radiation are pulsed, and said controller is configured to vary the pulse frequency or pulse duration of said beams of electromagnetic radiation in relation to the velocity at which said beams traverse the surface of said region of skin.

29. The apparatus of any one of paragraphs 17 to 28 wherein said beams of electromagnetic radiation are spaced such that said plurality of micro-lines of damaged tissue cover approximately 50%, 40%, 30%, or 20% of the surface of said region of skin being treated.

30. The apparatus of any one of paragraphs 17 to 29 wherein said housing further comprises a handle and is configured to be manually traversed over said region of skin being treated to form said micro-lines of damaged tissue.

31. The apparatus of any one of paragraphs 17 to 30 further comprising a scanning means configured to scan said beams of electromagnetic radiation over a region of skin to be treated to create a plurality of micro-lines of damaged tissue, with said housing being held essentially stationary relative to said region of skin being treated.

32. The apparatus of any one of paragraphs 17 to 31 wherein said housing further comprises conductive cooling means capable of cooling the surface of said skin being treated before or during the creation of said micro-lines of damaged tissue.

33. The apparatus of any one of paragraphs 17 to 32 wherein said housing further comprises convective cooling means capable of cooling the surface of said skin being treated before or during the creation of said micro-lines of damaged tissue.

34. An apparatus for treating skin, comprising:
 a housing;
 a mounting surface attached to said housing; and
 a plurality of essentially parallel blades fixed to said mounting surface, wherein said blades are configured to protrude from said mounting surface and penetrate the skin to create a plurality of micro-lines of damaged tissue when said housing is translated over a region of skin being treated.

35. The apparatus of paragraph 34 wherein said blades comprise diamond knives, microblades, or scalpels.

36. The apparatus of paragraph 34 or 35 wherein said blades are configured to penetrate into said skin to a depth of up to 1000 µm, up to 300 µm, up to 100 µm, or up to 50 µm, when said housing is translated over said region of skin being treated.

37. The apparatus of paragraph 36 wherein the maximum width of said blades is approximately 30 µm, approximately 60 µm, approximately 80 µm, approximately 120 µm, or approximately 400 µm.

38. The apparatus of paragraph 37 wherein the spacing between the nearest sides of adjacent blades is approximately 30 µm, approximately 60 µm, approximately 80 µm, approximately 120 µm, or approximately 400 µm.

39. The apparatus of any one of paragraphs 34 to 38 wherein said mounting surface further comprises conductive cooling means configured to contact the surface of said region of skin being treated when said essentially parallel blades are penetrating said skin.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for treating a region of a skin, comprising:
 generating a plurality of continuous micro-lines of damaged tissue in the region of the skin;
 wherein at least two adjacent ones of the micro-lines are substantially parallel to one another, and are separated from one another by an undamaged tissue region, wherein the micro-lines extend from a surface of the region of the skin through an epidermis of the skin and into a dermis of the skin, and wherein the micro-lines extend laterally along at least a portion of the surface of the region of skin.

2. The method of claim 1, wherein a width of the micro-lines is between approximately 10 µm and approximately 1 mm.

3. The method of claim 2, wherein a width of the undamaged tissue region is between approximately 10 µm and approximately 1 mm.

4. The method of claim 3, wherein a length of the micro lines as measured along the surface is at least about four times as large as a width of the micro-lines as measured along the surface.

5. The method of claim 3, wherein the at least one particular depth is between approximately 50 µm and approximately 1000 µm.

6. The method of claim 3, wherein the at least one particular depth is between approximately 60 µm and approximately 120 µm.

7. The method of claim 3, wherein the width of the undamaged tissue region is between approximately 30 µm and approximately 400 µm.

8. The method of claim 3, wherein the width of the undamaged tissue region is between approximately 60 µm and approximately 120 µm.

9. The method of claim 3, wherein the width of the undamaged tissue region is approximately the same as the width of a contiguous micro-line.

10. The method of claim 3, wherein the width of the undamaged tissue region is approximately twice as large as the width of any one of the micro-lines.

11. The method of claim 3, wherein the micro-lines are generated in a form of at least one of approximately parallel straight lines, approximately parallel curved lines, or approximately parallel wavy lines.

12. The method of claim 3, further comprising cooling at least one portion of the region of the skin at least one of before or during the generation of the plurality of micro-lines.

13. The method of claim 3, wherein the micro-lines are effectuated using an electromagnetic source configured to provide one or more beams of an electromagnetic radiation.

14. The method of claim 13, wherein a wavelength of the electromagnetic radiation is between approximately 400 nm and approximately 1000 nm.

15. The method of claim 13, wherein a wavelength of the electromagnetic radiation is between approximately 1200 nm and approximately 2300 nm.

16. The method of claim 13, wherein the electromagnetic source comprises at least one of a laser, a diode laser, an ER:YaG laser, a Nd:YaG laser, an argon-ion laser, a He—Ne laser, a carbon dioxide laser, an excimer laser, or a ruby laser.

17. The method of claim 16, wherein the one or more beams of the electromagnetic radiation are provided using a beam splitting arrangement.

18. The method of claim 3, wherein the micro-lines are effectuated using at least one of a plurality of blades, a plurality of scalpels, or a plurality of diamond knives.

19. A method for treating a region of a skin, comprising:
 generating a plurality of continuous micro-lines of damaged tissue in the region of the skin, wherein at least two adjacent ones of the micro-lines are substantially parallel to one another, and are separated from one another by an undamaged tissue region, wherein the micro-lines extend from a surface of the region of the skin through an epidermis of the skin and into a dermis of the skin, and wherein a length of the micro-lines as measured along the surface is at least about four times as large as a width of the micro-lines as measured along the surface.

20. The method of claim 19, wherein the width of the micro-lines is between approximately 10 μm and approximately 1 mm.

21. The method of claim 20, wherein a width of the undamaged tissue region is between approximately 10 μm and approximately 1 mm.

22. The method of claim 21, wherein the at least one particular depth is between approximately 50 μm and approximately 1000 μm.

23. The method of claim 21, wherein the micro-lines are effectuated using an electromagnetic source configured to provide one or more beams of an electromagnetic radiation.

24. The method of claim 23, wherein the electromagnetic source comprises at least one of a laser, a diode laser, an ER:YaG laser, a Nd:YaG laser, an argon-ion laser, a He—Ne laser, a carbon dioxide laser, an excimer laser, or a ruby laser.

25. The method of claim 21, wherein the micro-lines are effectuated using at least one of a plurality of blades, a plurality of scalpels, or a plurality of diamond knives.

* * * * *

UNITED STATES PATENT AND TRADEMARK OFFICE
CERTIFICATE OF CORRECTION

| | | |
|---|---|---|
| PATENT NO. | : 7,942,153 B2 | Page 1 of 1 |
| APPLICATION NO. | : 11/931232 | |
| DATED | : May 17, 2011 | |
| INVENTOR(S) | : Dieter Manstein et al. | |

It is certified that error appears in the above-identified patent and that said Letters Patent is hereby corrected as shown below:

Title Page,
Insert the "RELATED U.S. APPLICATION DATA" section with the following paragraph as follows:

--Division of application no. 11/097,825, April 1, 2005, issued as Patent no. 7,331,953, which claims benefit of application no. 60/558,397 April 1, 2004, and claims benefit of application no. 60/558,476, April 1, 2004--

Signed and Sealed this
Twenty-second Day of November, 2011

David J. Kappos
*Director of the United States Patent and Trademark Office*